US00PP14840P2

(12) United States Plant Patent
Bessho

(10) Patent No.: US PP14,840 P2
(45) Date of Patent: Jun. 1, 2004

(54) CALIBRACHOA PLANT NAMED 'KAKEGAWA S54'

(50) Latin Name: *Calibrachoa sp.*
Varietal Denomination: Kakegawa S54

(75) Inventor: Masao Bessho, Kakegawa (JP)

(73) Assignee: Sakata Seed Corporation (JP)

( * ) Notice: Subject to any disclaimer, the term of this patent is extended or adjusted under 35 U.S.C. 154(b) by 5 days.

(21) Appl. No.: 10/401,814

(22) Filed: Mar. 28, 2003

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette Para
(74) *Attorney, Agent, or Firm*—Jondle & Associates PC

(57) ABSTRACT

'Kakegawa S54' is a new variety of Calibrachoa plant. This new variety has rose-pink colored flowers and dark green foliage.

1 Drawing Sheet

Botanical classification: Calibrachoa sp.
Variety denomination: 'Kakegawa S54'.

BACKGROUND OF THE INVENTION

'Kakegawa S54' originated from a hybridization made in November 1998 in Kakegawa, Japan. The female parent was a Calibrachoa breeding line with bluish red colored flowers and erect habit known as K7-1159. The male parent was a Calibrachoa breeding line with white flowers and a ring at the corolla throat and creeping plant habit known as 97-1101-1.

In February 1999, $F_1$ seed was sown from this cross and 30 plants were transplanted to outdoors. Three plants were selected and intercrossed to produce $F_2$ seed. In August 1999 the second generation seed was planted in the field at Kakegawa and plants with different shades of pink flowers and white and pink flowers with or without corolla throat markings were observed. One plant with bluish pink petals and a yellow corolla tube was selected. The selection was vegetatively propagated again in February 2000 and evaluated in greenhouses in Japan.

The breeder selected one line, for its flower color and abundance, to be vegetatively propagated and further evaluated in Salinas, Calif. during 2001. This selection was subsequently named 'Kakegawa S54' and was determined to have its trait characteristics firmly fixed.

DESCRIPTION OF PHOTOGRAPH

This new Calibrachoa plant is illustrated by the accompanying photographs which show blooms, and foliage of the plant in full color, the colors shown being as true as can be reasonably obtained by conventional photographic procedures.

Figure 1:
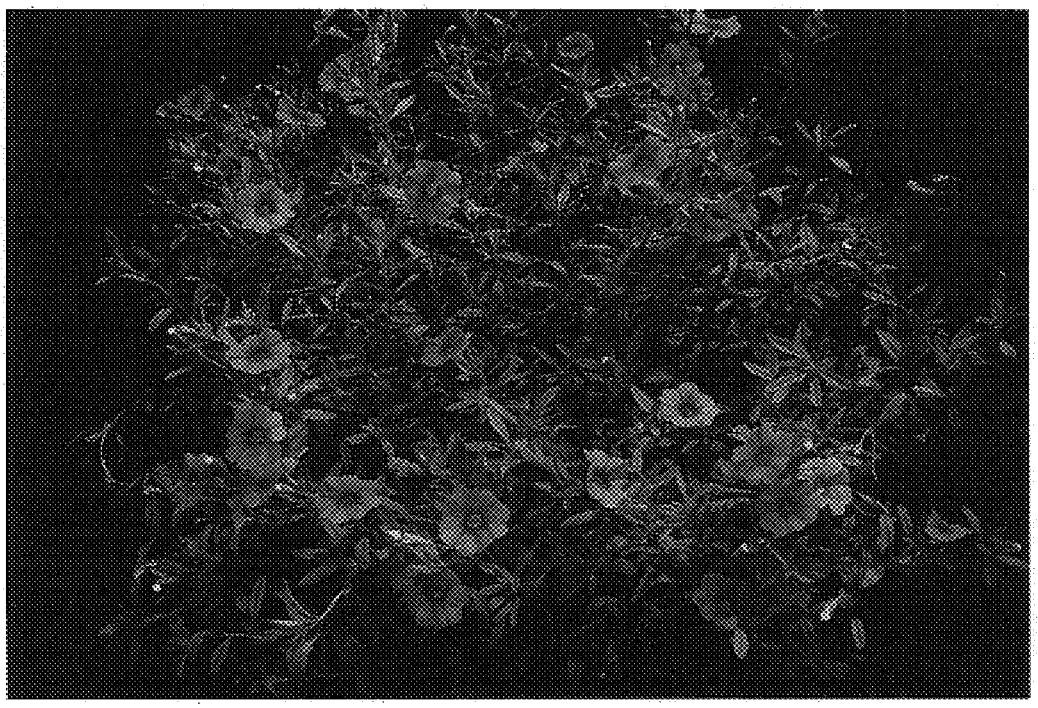

FIG. 1 shows the entire plant shows.

Figure 2:
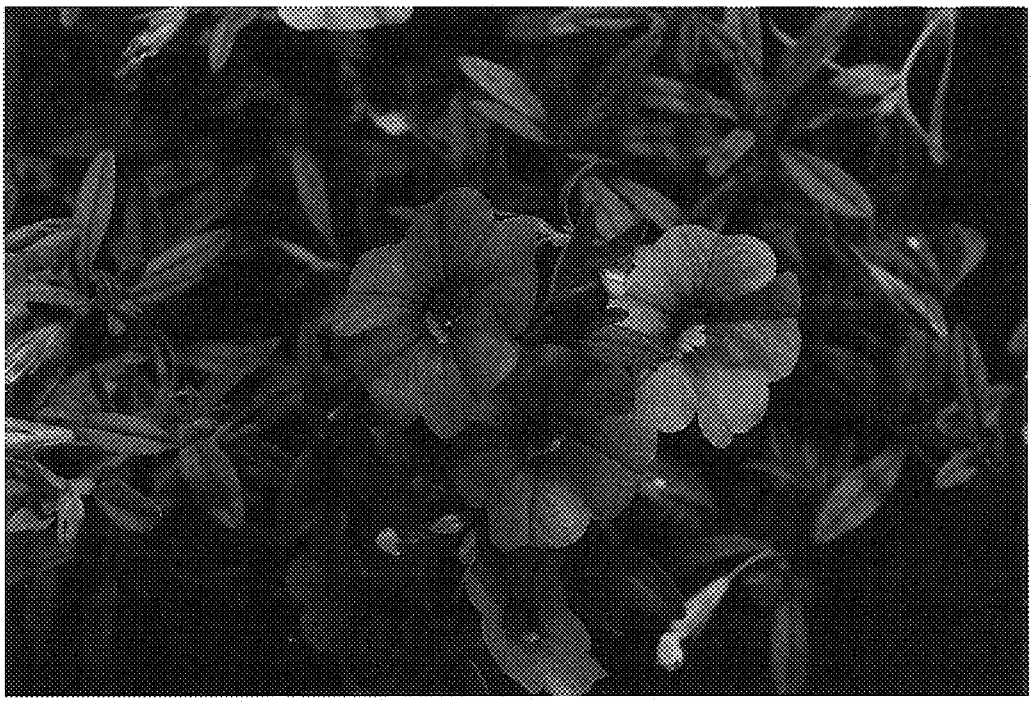

FIG. 2 the mature inflorescence.

DESCRIPTION OF THE GENUS CALIBRACHOA LLAVE & LEX

The genus Petunia was originally established in 1803 by A. L. Jussieu, who described both *P. parviflora* and *P. nyctaginifloa* as type species. Using a non-horticultural system that selected the first mentioned species as the type species (lectotype), N. L. Britton and H. A. Brown declared *P. parviflora* as the type species for Petunia in 1913.

During the 1980's and 1990, H. J. Wijsman published a series of articles regarding the ancestry of P. hybrida, the Garden Petunia, and the inter-relationship of several species classified as Petunia. These studies discovered that P. hybrida and its ancestrial species, *P. nyctaginiflora* (=*P. axillaris*) and *P. violacea* (=*P. integrifolia*), possessed 14 pairs of chromosomes while several other species, including *P. parviflora*, possessed 18 pairs of chromosomes. Since *P. parviflora* was the lectotype species for the Petunia genus, Wijsman and J. H. de Jong proposed transferring the 14 chromosome species to the genus Stimoryne. Horticulturists opposed reclassifying the Garden Petunia and in 1986, Wijsman proposed the alternative of making *P. nyctaginiflora* the lectotype species for Petunia and transferring the 18 chromosome species to another genus. The I. N. G. Committee adopted this proposal. By 1990 Wijsman had transferred several species, including *P. parviflora* (=*C. parviflora*) to Calibrachoa, originally established by Llave and Lexarza in 1825. *Calibrachoa parviflora* (=*C. mexicana* Llave & Lexarza) is now the type species for the genus Calibrachoa.

Classification of the current Petunia and Calibrachoa species is still in progress. New species are also being identified. Consequently a proper description has not been written for the Calibrachoa genus. Calibrachoa can, however, be distinguished from Petunia based on the higher chromosome number, chromosome morphology, plant branching habit and type of flower bud aestivation. Whereas Petunia species bear a flower peduncle and one new stem from a node, Calibrachoa bear a flower peduncle and three stems. Petunia species have a cochlear corolla bud, a single outermost petal covers the other four, radially folded and terminally contorted petals. Calibrachoa flower buds are flat with all five petals linearly folded and the two lower petals forming a cover around the three other petals and fused together.

ENVIRONMENTAL CONDITIONS FOR PLANT GROWTH

The terminal 1.0 to 1.5 inches of an actively growing stem was excised. The base of the cuttings were dipped for 1 to 2 seconds in a 1:9 solution of Dip 'N Grow (1 Dip 'N Grow:

9 water) root inducing solution immediately prior to sticking into the cells trays. Cuttings were stuck into plastic cell trays having 98 cells, and containing a moistened peat moss-based growing medium. The cuttings were misted with water from overhead for 10 seconds every 30 minutes until sufficient roots were formed. The vegetative cuttings were propagated in five to six weeks.

Rooted cuttings were transplanted and grown in 20 cm diameter plastic pots in a glass greenhouse. Pots contained a peat moss-based growing medium. Soluble fertilizer containing 20% nitrogen, 10% phosphorus and 20% potassium was applied once a day or every other day. Fertilizer was applied in irrigation water. Pots were top-dressed with a slow release fertilizer containing 20% nitrogen, 10% phosphorus and 18% potassium. The typical average air temperature was 24C.

DETAILED DESCRIPTION OF THE NEW PLANT

The following traits and characteristics describe the new variety.

Classification:
- *Family.*—Solanaceae.
- *Species.*—Calibrachoa spp.
- *Common names.*—Petunia.

Parentage:
- *Female parent.*—Breeding line K7-1159. (Not patented).
- *Male parent.*—Breeding line 97-1101-1. (Not patented).

Growth:
- *Habit.*—Decumbent mounding in center.
- *Height.*—23.0 cm.
- *Spread.*—115.0 cm when grown in a 41 cm hanging basket or pot, and using five 20 cm potted plants in one hanging basket.
- *Life cycle.*—Annual.
- *Time to produce a rooted cutting.*—3 weeks.
- *Time to bloom from propagation.*—10 weeks.
- *Flowering season.*—Spring and summer.
- *Flowering requirements.*—No particular requirements, day neutral.
- *Resistance/susceptibility.*—Excellent resistance to rain, heat and drought. Will not tolerate temperatures below 10C. Plants are susceptible to Botrytis, powdery mildew, various stem and root rots, and certain viruses, like Tobacco Mosaic Virus and Impatiens Necrotic Spotted Virus. Plants can be infested with aphids, leafminer, whitefly and various Lepitopdera.
- *Form.*—Branching, dense.

Stems:
- *Stem color.*—R.H.S. 138B (green).
- *Anthocyanin color.*—RHS N77A (purple).
- *Pubescence.*—Heavy.
- *Pubescence color.*—Clear
- *Pubescence shape.*—Pointed.
- *Stem description.*—Round, slightly ancipital.
- *Stem diameter.*—1.5 mm.
- *Internode length.*—1.5 to 2.5 cm.

Leaves:
- *Leaf tip.*—Mucronate.
- *Leaf arrangement.*—Alternate.
- *Leaf base.*—Decurrent.
- *Leaf color.*—*Upper surface: R.H.S.* 139A (green); lower surface: R.H.S. 139A (green).
- *Leaf fragrance.*—Absent.
- *Leaf margin.*—Entire.
- *Leaf surface.*—Rough.
- *Leaf surface pubescence.*—Slight.
- *Leaf variegation.*—No.
- *Leaf length.*—2.5 cm.
- *Leaf shape.*—Elliptical.
- *Leaf width.*—8.0 mm.

Flowers:
- *Calyx.*—5 sepals; 8.0×2.0 mm (l×w); free.
- *Corolla.*—5 petals, fused.
- *Flower diameter.*—3.5 cm.
- *Bud color.*—R.H.S. 150C (yellow-green).
- *Bud shape.*—Ovate.
- *Bud surface.*—Pubescent.
- *Ovary.*—Superior.
- *Duration of flower life.*—5 days.
- *Flowering habit.*—Indeterminate.
- *Placenta arrangement.*—Central.
- *Peduncle size.*—1.0 mm diameter; 1.5 cm length.
- *Inflorescence type.*—Solitary.
- *Stamens.*—Free.
- *Stamen color.*—R.H.S 1B (green-yellow).
- *Stigma color.*—R.H.S. 143B (green).
- *Style color.*—R.H.S. 142C (green).
- *Petal size.*—1.5 cm ×1.7 cm (1×w).
- *Petal color.*—Upper surface: R.H.S. N74C (red-purple) with R.H.S. N74B (red-purple) petal mid-vein and corolla throat; lower surface: R.H.S. N74B (red-purple); corolla tube: inner surface: R.H.S. 6D (yellow) with R.H.S. 74B (red-purple) veins; outer surface: R.H.S. 6D (yellow).
- *Petal pubescence.*—Glabrous.
- *Pollen color.*—R.H.S. 9A (yellow).
- *Produces seed.*—None.

COMPARISON WITH MOST SIMILAR VARIETY

'Kakegawa S54' is a distinct variety of Calibrachoa owing to its rose-pink flower with bright yellow tube and dark rose corolla throat and petal mid veins. 'Kakegawa S54' is most similar to the variety Colorburst Rose (U.S. Plant Pat. No. 12, 147P2) however there are numerous differences as shown in the table below.

| Characteristic | 'Kakegawa S54' | 'Colorburst Rose' |
|---|---|---|
| Stem Pubescence | Slight | Heavy |
| Bud Color | RHS 150C (yellow-green) | RHS 74B (red-purple) |
| Petal Color (upper) | RHS N74C (red-purple) | RHS 74B (red-purple) |
| Pollen Color | RHS 9A (yellow) | RHS 13B (yellow) |
| Stamen Color | RHS 1B (green-yellow) | RHS 145C (yellow-green) |
| Style Color | RHS 142C (green) | RHS 149B (yellow-green) |

What is claimed is:

1. A new and distinct Calibrachoa plant as shown and described herein.

* * * * *